United States Patent [19]
Molina

[11] 3,975,634
[45] Aug. 17, 1976

[54] WATER WASHABLE DYE PENETRANT COMPOSITION AND METHOD UTILIZING SAME

[75] Inventor: Orlando G. Molina, Westminster, Calif.

[73] Assignee: Rockwell International Corporation, El Segundo, Calif.

[22] Filed: May 22, 1975

[21] Appl. No.: 580,105

Related U.S. Application Data

[62] Division of Ser. No. 444,432, Feb. 21, 1974, Pat. No. 3,915,885.

[52] U.S. Cl. .............................. 250/302; 73/104; 252/301.19
[51] Int. Cl.² ........................................ G01N 21/16
[58] Field of Search ............. 250/302; 252/301.2 P; 73/104

[56] References Cited
UNITED STATES PATENTS

| | | | |
|---|---|---|---|
| 2,953,530 | 9/1960 | Switzer | 250/302 X |
| 3,716,492 | 2/1973 | Graham | 250/302 X |
| R26,888 | 5/1970 | Alburger | 250/302 X |

*Primary Examiner*—Archie R. Borchelt
*Attorney, Agent, or Firm*—Charles T. Silberberg; L. Lee Humphries

[57] ABSTRACT

A water washable substantially biodegradable dye penetrant composition having good sensitivity and high stability, for use in non-destructive testing of objects to locate voids and defects therein, said composition consisting essentially of an organic dye, preferably a fluorescent dye, and a carrier or solvent for said dye, in the form of certain straight chain, primary, aliphatic oxyalkylated alcohols, particularly the biodegradable surfactants comprised of the nonionic condensation products of linear primary aliphatic alcohols having from 10 to 18 carbon atoms, with ethylene oxide and propylene oxide, preferably in the form of a mixture thereof. In the method of application of the dye penetrant composition, such composition is applied to the surface of an object containing cracks and flaws, water is applied to the surface of the object to remove excess liquid dye penetrant composition from the surface without removing such penetrant from the cracks and defects, and with or without a developer, the surface of the object is viewed under suitable lighting conditions, e.g. ultraviolet or black light when the dye in the penetrant is a fluorescent dye, to locate any cracks or defects in the surface of the body as indicated by colored traces from the dye penetrant remaining in the cracks and flaws.

13 Claims, No Drawings

WATER WASHABLE DYE PENETRANT COMPOSITION AND METHOD UTILIZING SAME

This is a division, of application Ser. No. 444,432 filed Feb. 21, 1974, now U.S. Pat. No. 3,915,885.

BACKGROUND OF THE INVENTION

This invention relates to an improved dye penetrant composition and method for non-destructively testing material specimens to locate and identify surface voids, cracks or defects, and more particularly to an improved liquid vehicle for such a dye penetrant. The invention is especially concerned with a novel easily water washable, stable and sensitive dye penetrant composition of the above type employing as solvent or vehicle essentially a biodegradable nonionic surfactant in the form of certain oxyalkylated alcohols; and to a method utilizing such dye penetrant composition for non-destructive testing of parts.

In known penetrant inspection methods for rapid location and evaluation of surface flaws or cracks in test bodies or parts, a dye penetrant composition, preferably containing a fluorescent dye, and which will penetrate the openings of the surface cracks or flaws in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks or surface flaws, to be drawn up out of the surface defects by capillary action. The part is then exposed to appropriate lighting conditions, such as invisible fluorescigenous light, and the location of the surface flaws is revealed by the emission of visible fluorescent light by the penetrant dye which was retained in the cracks or flaws after the penetrant composition was removed from the surface of the part.

For best efficiency, particularly for the detection and location of minute surface cracks and flaws, it is necessary that the dye penetrant composition have high sensitivity.

Volatile type solvents are commonly employed for extending or thinning dye penetrant inspection solutions or compositions. This is done chiefly for the purpose of lowering the viscosity of the penetrant in order to adapt it for application in spraying systems. Thus for example solvents such as kerosene, light fuel oils, and methyl ethyl ketone, all highly volatile solvents, have heretofore been employed in prior art dye penetrants. See for example U.S. Pat. No. 2,806,959. Further, most dye penetrant solutions in practice generally require the use of a combination of solvents, including primary and secondary solvents, extender solvents and wetting agents.

However, the use of volatile solvents in dye penetrant compositions has certain disadvantages. Thus, the use of volatile solvents in dye penetrants results in the evolution of fumes and solvent vapors which are rapidly formed by the evaporating solvent.

In addition, stability of the penetrant solution is essential without the necessity for carefully balancing the various liquid components of a dye penetrant solution in order to obtain efficient penetration of the solution into the cracks and flaws of a part, dye solubility, wetting action and washability control.

An additional criterion has recently developed also with respect to dye penetrant solutions and compositions. Generally, dye penetrant solutions presently being used and containing solvents and wetting agents present a disposal problem and hence the necessity for the development of dye penetrant solutions and compositions which are biodegradable, that is which employ dye solvents and carriers which are biodegradable, and are readily available despite the petrochemical shortage, has attained considerable importance.

Accordingly, an object of the present invention is the provision of a readily water washable dye penetrant solution or composition which avoids the use of the conventional volatile solvents and wetting agents and their above-noted disadvantages, and which is highly stable, has good sensitivity and is essentially non-flammable and non-toxic. A particular object of the invention is to provide a dye penetrant solution of the above-noted type, having good wettability characteristics, and which employs a single dye solvent or carrier which is readily available and is biodegradable, thus rendering the dye penetrant solution essentially biodegradable.

DESCRIPTION OF THE INVENTION

The above objects and advantages are accomplished according to the invention by providing a dye penetrant composition containing a dye, e.g. a fluorescent dye, in a solvent or carrier for such dye, which is a biodegradable nonionic surfactant in the form of certain oxyalkylated alcohols, and particularly the biodegradable surfactants comprised of nonionic condensation products of certain linear primary aliphatic alcohols with ethylene oxide and propylene oxide, as described in greater detail hereinafter. This unique dye penetrant composition provides a single or "one liquid" dye penetrant solution, in that it does not require the presence of any additional solvents or wetting agents, generally employed in prior art dye penetrant solutions and compositions. The dye penetrant solution of the invention is accordingly very simple to mix, and to use, is economical, and not only is biodegradable, but the above-noted nonionic solvent carrier for the dye is readily available since it is less dependent on petrochemical sources for its manufacture.

Thus, it has been found according to the present invention that the simple addition of a small amount of dye, preferably in proportions hereinafter disclosed, to the above-noted nonionic oxyalkylated alcohols results in an efficient powerful dye penetrant with highly unique and desirable characteristics including instant washability from the surface of parts without loss of dye penetrant solution entrapped within the defects and cracks. Such dye penetrant solution penetrates the cracks and flaws in the surface of parts instantly and without having to wait for relatively long periods for this purpose as in the case of many commercial penetrants. Thus, the invention provides a dye penetrant solution employing a single carrier or vehicle for the dye, while at the same time obtaining high stability of the dye in the carrier, and also obtaining excellent wettability and instant washability of the dye penetrant solution from the part surface without dislodging the dye penetrant from the cracks and flaws in a part surface. Since the above-noted nonionic dye solvent or carrier employed has extremely low volatility it provides uniform and stable dye sensitivity. Further, the nonionic solvent or carrier of the dye penetrant solution hereof has a high flash point and is essentially non-flammable, is substantially odorless, and of particular significance, it is biodegradable.

The nonionic biodegradable solvent or carrier for the dye according to the invention are alkylene oxide condensation products prepared by the reaction of an organic compound having a reactive hydrogen atom, such as an aliphatic alcohol, with ethylene oxide, propylene oxide, or mixtures thereof. More particularly, such nonionic solvents or carriers can be defined as straight chain, primary, aliphatic oxyalkylated alcohols, generally in the form of mixtures thereof, wherein the primary aliphatic alcohols can have from 8 to 20 carbon atoms, preferably 10 to 18 carbon atoms, and the oxyalkyl groups are ethylene oxide and propylene oxide, preferably in the form of a mixture thereof.

One preferred class of nonionic carriers within the broad class of materials defined above is a cogeneric mixture of compounds represented by the formula:

$$R-O(A)H$$

wherein:

R is an essentially linear alkyl group having from ten to eighteen carbon atoms, with the proviso that at least 70 weight percent of said compounds in said mixture have an R of from twelve to sixteen carbon atoms, and A is a mixture of oxypropylene and oxyethylene groups, said oxypropylene and oxyethylene groups being from 55% to 80% of the total weight of the compounds, the oxypropylene to oxyethylene ratio of said total weight being from 0.85:1 to 2.75:1, preferably 1.25:1 to 2.25:1.

Another preferred class of condensation products or oxyalkylated alcohols within the above definition are those wherein the aliphatic alcohols of the oxyalkylated alcohols, or R in the above formula, ranges from 12 to 18 carbon atoms, and the total number of ethylene oxide and proylene oxide groups in the mixture thereof, or designated A in the above formula, ranges from about 4 to about 14.

The term "cogeneric mixture" as employed herein, designates a series of closely related homologues obtained by condensing a plurality of oxide units, with an alcohol or a mixture thereof. As is known, when a mixture of this type is generated, various oxyalkylene chain lengths are obtained.

Alcohols which may be employed in the preparation of the products noted above are those essentially linear, primary, aliphatic alcohols having from 8 to 20 carbon atoms, preferably 10 to 18 carbon atoms. Mixtures of alcohols are usually preferred since their use provides for a good balance of properties in the resulting products. Examples of alcohols which are operable include decyl alcohol, undecyl alcohol, lauryl alcohol, tridecyl alcohol, tetradecyl alcohol, pentadecyl alcohol, cetyl alcohol, heptadecyl alcohol, stearyl alcohol, hydrogenated tallow alcohol, and mixtures thereof. They may be naturally-derived such as from coconut oil or synthetically-derived such as from linear alkanes or linear olefins.

The nonionic biodegradable surfactants employed as carrier or vehicle for the dye of the penetrant solution according to the invention, are prepared by condensing an alcohol or mixture of alcohols, as described above, with a mixture of ethylene oxide and propylene oxide, in the presence of an alkaline catalyst, such as potassium hydroxide. The oxide mixture may be added to the alcohol in one continuous step or it may be added in several steps. The products thus produced possess random distribution of oxyethylene and oxypropylene groups.

The nonionic surface active agents described above and their method of preparation are disclosed in U.S. Pat. No. 3,504,041, and such disclosure is incorporated herein by reference. These surface active agents are believed to include, for example, that class of surfactants which are marketed as the Plurafac surfactants PA-40 grades. It is noted that these surfactants are disclosed in the above patent as rinse additives in automatic dishwashing machines.

Another class of biodegradable liquid, water miscible oxyalkylated alcohol condensation products within the above definition are those wherein the aliphatic alcohol, or R, is a straight chain alkyl group having from 8 to 20 carbon atoms, the number of ethylene oxide groups in the mixture thereof with propylene oxide, or A, ranges from 3.75 to 12.75, and the number of propylene oxide groups in such mixture ranges from 1.7 to 7.0, the oxyethylene to oxypropylene ratio in such mixture being from 1.8:1 to 2.2:1. Such cogeneric mixtures can be prepared in two steps, the first step being condensation of an alcohol mixture and ethylene oxide in the presence of an alkaline condensing agent or catalyst, to form an ethoxylated product, followed by condensing the resulting ethoxylated product with propylene oxide. There can be employed in such reaction a mixture of straight chain aliphatic alcohols having from 8 to 20 carbon atoms in the aliphatic chain, said mixture containing from 0 to 10 weight percent of an alcohol having 8 carbon atoms, 0 to 50 weight percent of an alcohol having 10 carbon atoms, 0 to 95 weight percent of an alcohol having 12 carbon atoms, 0 to 95 weight percent of an alcohol having 14 carbon atoms, 0 to 95 weight percent of an alcohol having 16 carbon atoms, 0 to 50 weight percent of an alcohol having 18 carbon atoms, and 0 to 10 weight percent of an alcohol having 20 carbon atoms. This cogeneric mixture of condensation products and the method of their preparation are disclosed in U.S. Pat. No. 3,340,309, and such disclosure is also incorporated herein by reference. The nonionic oxyalkylated alcohols marketed as the RA-20 grades of Plurafac, are believed representative of the class of surface active agents disclosed in the latter patent. The surfactants disclosed in the latter patent are also described as being rinse additives for automatic dishwashing machines.

Various other Plurafac grades which are marketed and are believed to be generally within the above-described classes of oxyalkylated alcohol surfactants are those designated RA-43, A-24, B-25.5, B-26 and D-25.

Any suitable dye generally employed in dye penetrant compositions can be incorporated into the nonionic oxyalkylated alcohol surfactants described above for producing the dye penetrant compositions of the invention. Preferably, however, a fluorescent dye is employed for this purpose. The oxyalkylated surfactant vehicle for the dye is compatible therewith and has the ability to dissolve either small or relatively large amounts of the dye and to hold a high concentration of dye in solution while providing good resolution and clarity of the dye trace in the cracks and flaws.

As previously noted, the dye penetrant solution employed according to the invention preferably contains a fluorescent dye. Various types of fluorescent dyes can be employed including for example the dye marketed as Fluorol 7CA as well as other fluorescent dyes such as those marketed as Calcofluor Yellow, Azosol Brilliant Yellow 6CF; Rhodanine B, Rhodanine 6 GDN, Calcofluor White RW, Blancophor White AW, Auramine and Eosine G, and water soluble fluorescent dyes such as Blanchophor FFG.

The dye penetrant composition employed according to the invention alternatively can contain non-fluorescent or daylight type dyes such as azo type dyes, e.g. xyleneazo-beta-naphthol, Mefford No. 322 dye, believed to be o-toluene-azoxyleneazo-beta-naphthol, and the azo dyes marketed as Oil Red O and Sudan Red. These dyes conveniently can be employed where daylight or white light is only available, and particularly where the surface of the body to be detected contains relatively gross cracks. However, it is preferred to employ fluorescent dyes having greater sensitivity or detectability as result of the high contrast obtained by the fluorescent indications.

The dye penetrant composition according to the present invention permits rapid and almost instantaneous removal or cleaning of the remaining dye penetrant from the object surface by water washing, e.g. by application of a water spray or a sprayed mixture of air and water, or by wiping with a water moistened cloth or a cloth moistened with a rapid drying solvent such as trichloroethane, without any need for emulsifiers and the like. Thus, the dye penetrant composition hereof has excellent wettability and practically instantaneous washability with water without removing dye penetrant from the cracks and defects on the part surface.

However, if desired, small amounts of extenders such as kerosene, and volatile solvents such as methyl ethyl ketone, isopropyl alcohol, and the like, can be added to the dye penetrant composition of the invention containing the oxyalkylated alcohol carrier, to vary the properties thereof. It is noted however that in preferred practice these additives are not employed and in effect a one liquid solution is provided according to the invention, in which the oxyalkylated alcohol surfactant is essentially the sole carrier for the dye.

The amount of dye which is incorporated into the oxyalkylated alcohol surfactant or carrier to produce the dye penetrant composition of the invention, can range from about 0.1 to 15, preferably about 0.5 to about 10, parts of the dye, or mixtures thereof, per 100 parts of the oxyalkylated alcohol surfactant, by weight. In preparing the dye penetrant composition of the invention, the dye is simply added to the oxyalkylated alcohol carrier, in the desired proportion. The resulting dye penetrant composition has high stability, the stability thereof being such that a test conducted by placing a dye penetrant solution represented by Composition I below, in a hot-air oven at 300°F for 16 hours did not reduce its performance and it had substantially less loss of solids by evaporation than a standard prior art penetrant solution subjected to the same test.

Where a developer composition is employed, any one of the three general types of developer compositions, namely, dry powder, wet aqueous (water-base) and wet nonaqueous (volatile solvent base) developer compositions can be employed. In each case, the developer composition contains a light colored powder, forming a coating which contrasts with the color of the dye in the penetrant and which acts as a wick or blotter, and causes liquid penetrant containing the dye, e.g. fluorescent dye, which was retained in the cracks or surface flaws, to be drawn up out of the surface defects by capillary action and to bleed through the powder. Preferred developer compositions for use in conjunction with the dye penetrant composition according to the invention, are those described in my copending application Ser. No. 212,799, filed Dec. 27, 1971, which is a dry powder developer containing fumed alumina, fumed silica, fumed titanium dioxide and talc, and in my U.S. Pat. No. 3,748,469, and which is a wet nonaqueous developer composition consisting essentially of isopropyl alcohol, talc and glycol monobutyl ether. The descriptions of such developer compositions contained in the above copending application and the above patent are incorporated herein by reference.

The following examples serve to illustrate but are not limitative of the benefits and advantages obtained by practice of the present invention.

EXAMPLE 1

The following liquid dye penetrant, designated composition I, was prepared:

| Composition I | Parts by Volume | Parts by Weight |
| --- | --- | --- |
| Plurafac A-24 | 22.5 | 99.0 |
| Calcofluor White RW | 2.0 | 5.0 |
| Fluorol 7 GA | .66 | 1.5 |
| Totals | 25.16 | 105.0 |

Plurafac A-24 is a straight chain, primary aliphatic oxyalkylated alcohol mixture believed to contain about 12 to about 18 carbon atoms in the alcohol chains, and a total of 4 to 14 oxyethylene and oxypropylene groups, generally as described in above U.S. Pat. No. 3,504,041.

The fluorescent dye penetrant composition I above was applied as by spraying, to one-half of the surface of a chromium-plated brass test panel containing minute cracks of the order of 0.00002 to 0.0001 inch in width, closely distributed over its entire surface. A water wash was then applied as by an air-water spray over the coating of the dye penetrant composition I on the test panel, causing instantaneous washing away of the dye penetrant on the surface of the panel without dislodging the dye penetrant from the surface cracks and thus entrapping the penetrant therein. It appeared that the above-noted Plurafac A-24 base penetrant has a high affinity for the cracks and defects in the panel surface, substantially greater than conventional dye penetrants.

The other half of the test panel surface was sprayed with a prior art fluorescent dye penetrant solution containing volatile ketone solvent and a phenyl polyethylene glycol ether surfactant, and required emulsifiers for removal of excess dye penetrant from the panel surface.

Both halves of the test panel surface to which penetrant composition I above and the prior art dye penetrant were initially respectively applied, were then covered with a powder developer having the following composition, according to my above copending application Ser. No. 212,799:

| COMPONENTS | Percent by weight |
| --- | --- |
| Talc | 52 |
| Alumina | 35 |
| Silica | 4 |
| TiO$_2$ | 9 |

The above developer was permitted to dwell over the two half surfaces of the test panel for a period of about 2 minutes.

Excess developer composition was then carefully removed from both half surfaces of the test panel by means of a gentle air blast.

The panel was then placed under black light (fluorescent) illumination and the respective half surfaces viewed in such illumination. It was observed that the first half side of the panel which had initially been treated with dye penetrant composition I of the invention, disclosed fluorescent indications from numerous readily defined microcracks therein, such fluorescent indications being substantially brighter and revealing a greater concentration of the microcracks than the fluorescent indications from the microcracks on the half side of the panel which has been initially treated with the prior art dye penetrant.

EXAMPLE 2

The sensitivity of the dye penetrant composition 1 of Example I above was reduced by adding one part by volume of Plurafac A-24 to 1 part by volume of composition I, designated Composition I', and by adding four parts of Plorafac A-24 to 1 part of composition I, and designated Composition I''.

Dye penetrant inspection tests were carried out in a manner generally similar to the procedure of Example 1, employing composition I' on a test panel containing cracks of intermediate size, and employing composition I'' on a test panel having gross microcracks.

In each of the two tests above, bright fluorescent indications were obtained from the cracks of intermediate size on the first panel, and from the gross microcracks on the second panel, employing compositions I' and I'', respectively, comparable to the brightness and sensitivity of the fluorescent indications obtained employing composition I in Example 1.

From Examples 1 to 2 above, it was observed that composition I functions as a high sensitivity dye penetrant formulation for detecting microcracks, dye penetrant composition 1' diluted with one part of Plurafac A-24, functions as a medium sensitivity dye penetrant for detecting intermediate size cracks, and dye penetrant composition I'', diluted with four parts of Plurafac A-24, functions as a low sensitivity dye penetrant for detecting gross microcracks. Thus there is provided according to the invention a dye penetrant which can be tailored for a large sensitivity range necessary to detect from the most minute microcrack to the largest gross crack, without requiring any change in the washability of the formulation. In other words, compositions I, I' and I'' above all have the same washability characteristics. On the other hand, it has been found from experience that commercial dye penetrants require penetrant solutions of different washability for controlling the entrappability of the penetrant inside of cracks, in order to provide different degrees of sensitivity. Thus, it is believed that the dye penetrant of the invention employing the above defined oxyalkylated alcohol surfactant carrier has the unique property of great affinity for remaining within the cracks and defects of a part, while that portion of the dye penetrant contacting the surface of the parts containing the cracks, can be instantaneously washed away with simple water spraying without dislodging the penetrant entrapments.

EXAMPLE 3

Tests on aluminum panels containing microcracks were carried out employing procedure similar to that employed in Example 1, utilizing composition I containing Plurafac A-24, and dye penetrant compositions similar to composition I, but containing in place of A-24, the Plurafacs B-25.5, B-26, D-25, RA-20, RA-30 and RA-40, respectively, on each of the panels.

Results obtained were similar to those obtained in Example I, but it appeared that the composition I containing Plurafac A-24 had the best all around performance, followed by that employing RA-40, although the dye penetrants containing the Plurafacs RA-20, RA-30 and D-25 provided brighter indications than that containing A-24.

It was also noted that RA-30 had substantially infinite water tolerance so that formulations of high sensitivity obtained with RA-30 can be further desensitized to any desired extent by addition of water instead of by addition of more RA-30 surfactant.

The above Plurafacs are understood to be of the class of surfactants disclosed in above U.S. Pat. Nos. 3,340,309 and 3,504,041, particularly the latter, comprised of the above defined oxyalkylated alcohols containing alkyl groups of from 10 to 18 carbon atoms, and 55 to 80% of the total weight, of oxypropylene and oxyethylene groups.

EXAMPLE 4

The following dye penetrant compositions are also illustrative of the dye penetrant solutions of the invention:

Table 1

| COMPONENTS | Parts by Weight | | | | |
| --- | --- | --- | --- | --- | --- |
| | II | III | IV | V | VI |
| Plurafac A-24, RA-20, RA-30 or RA-40 | 90 | 88 | 92 | 95 | 94 |
| Calcofluor White | 6 | 8 | — | — | 4 |
| Fluorol 7GA | 4 | 4 | 8 | 5 | 2 |

EXAMPLE 5

The procedure of Example 1 was essentially followed, but employing in place of composition I a non-fluorescent water washable biodegradable dye penetrant solution according to the invention, consisting of 15 parts of Plurafac A-24 and 1 part of Oil Red O dye, by volume, and employing a conventional non-fluorescent dye penetrant containing solvent and surfactant of the types noted in Example 1.

Excellent results of crack detectability were obtained employing such biodegradable non-fluorescent dye penetrant, as compared to the non-fluorescent prior art dye penetrant.

However, the brightness and sensitivity of the colored dye traces obtained employing the biodegradable nonfluorescent dye penetrant of this example were not as great as for the fluorescent biodegradable dye penetrant composition I.

EXAMPLE 6

The procedure of Example 1 was followed except that in place of the powder developer employed in Example 1, a nonaqueous developer having the following composition, according to my above U.S. Pat. No. 3,748,469 was employed:

| COMPONENTS | Percent by weight |
|---|---|
| Isoprypyl alcohol | 70.5 |
| Talc | 28.6 |
| Glycol monobutyl ether | 0.9 |

The above developer was permitted to remain on the panel surfaces to which it was applied for a period of 2 minutes, until substantially all of the isopropyl alcohol had evaporated and a substantially dry powder coating was formed.

Results similar to the results of Example 1 were obtained.

From the foregoing, it is seen that the invention provides a highly effective substantially biodegradable water washable dye penetrant composition employing substantially a single carrier in the form of certain axyalkylated alcohols, which permits substantially instantaneous removal of dye penetrant from the surface of the part in a single wash operation, while maintaining the dye penetrant in the cracks or defects of the part, followed by further processing of the dye penetrant coating as desired in the conventional manner for viewing under suitable e.g. fluorescent, lighting conditions, to obtain improved brilliance, definition and resolution of dye traces from cracks and flaws in the part surface, as compared to prior art penetrants, and affording a dye penetrant composition having a wide range of sensitivity, and avoiding the use of volatile extenders and thinners in the dye penetrant.

Since various changes and modifications of the invention will occur to and can be made readily by those skilled in the art without departing from the invention concept, the invention is not to be taken as limited except by the scope of the appended claims.

I claim:

1. A method for detecting cracks and flaws in the surface of an object, which comprises applying to said surface a water washable biodegradable liquid dye penetrant composition which contains essentially of (1) a nonionic surfactant in the form of a mixture of straight chain, primary, aliphatic oxyalkylated alcohols, wherein said alcohols can have from 8 to 20 carbon atoms and the oxyalkyl groups are a mixture of ethylene oxide and propylene oxide groups, and (2) a small amount of a dye soluble in said surfactant; removing said dye penetrant composition from said surface without removing said dye penetrant composition from said cracks and flaws in said surface, and viewing the surface of said object under lighting conditions to obtain colored traces from the dye in said cracks and flaws.

2. A method as defined in claim 1, said liquid dye penetrant composition consisting essentially of said nonionic surfactant as the sole liquid carrier for said dye.

3. A method as defined in claim 1, said removal of said dye penetrant composition being carried out by application of a water wash over said surface.

4. A method as defined in claim 3, said water wash being carried out by spraying water over said surface.

5. A method as defined in claim 1, wherein said dye is a fluorescent dye and said surface of said object is viewed under fluorescigenous light to obtain colored fluorescent traces from the dye in said cracks and flaws.

6. A method as defined in claim 1, including applying a developer to said surface after removing said dye penetrant composition from said surface and prior to said viewing the surface of said object.

7. A method as defined in claim 1, wherein said surfactant is a cogeneric mixture of compounds having the formula:

$$R - O(A)H$$

wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and said dye is present in said composition in an amount ranging from about 0.1 to 15 parts per 100 parts, by weight, of said surfactant.

8. A method as defined in claim 1, wherein said aliphatic alcohols of said surfactant can have from 12 to 18 carbon atoms, and the total number of ethylene oxide and propylene oxide groups can range from about 4 to about 14; and said dye is present in said composition in an amount ranging from about 0.1 to 15 parts, per 100 parts, by weight, of said surfactant.

9. A method as defined in claim 7, wherein said dye is a fluorescent dye and said surface of said object is viewed under fluorescigenous light to obtain colored fluorescent traces from the dye in said cracks and flaws.

10. A method as defined in claim 8, wherein said dye is a fluorescent dye and said surface of said object is viewed under fluorescigenous light to obtain colored fluorescent traces from the dye in said cracks and flaws.

11. A method as defined in claim 10, said removal of said dye penetrant composition being carried out by application of a water wash over said surface.

12. A method as defined in claim 10, said removal of said dye penetrant composition being carried out by wiping said surface with a water moistened cloth.

13. A method as defined in claim 10, said removal of said dye penetrant composition being carried out by wiping said surface with a cloth moistened with a rapid drying solvent.

* * * * *